US00PP15226P2

(12) United States Plant Patent
Tate

(10) Patent No.: US PP15,226 P2
(45) Date of Patent: Oct. 12, 2004

(54) SHUMARD OAK TREE NAMED 'ACNRT1'

(50) Latin Name: *Quercus Shumardii*
Varietal Denomination: ACNRT1

(76) Inventor: Ray Tate, 435 Ray's Church Rd., Bishop, GA (US) 30621

( * ) Notice: Subject to any disclaimer, the term of this patent is extended or adjusted under 35 U.S.C. 154(b) by 39 days.

(21) Appl. No.: 10/641,717

(22) Filed: Aug. 15, 2003

(51) Int. Cl.[7] ..... A01H 5/00

(52) U.S. Cl. ..... Plt./225

(58) Field of Search ..... Plt./225

*Primary Examiner*—Anne Marie Grunberg
*Assistant Examiner*—Annette H Para
(74) *Attorney, Agent, or Firm*—Polster, Lieder, Woodruff & Lucchesi, L.C.

(57) ABSTRACT

A Shumard Oak tree named 'ACNRT1' and distinguished by having an upright, well-branched central leader and also capable of being reliably reproduced from vegetative cuttings.

4 Drawing Sheets

Latin name of the genus and species of the plant claimed: *Quercus Shumardii.*
Variety denomination: 'ACNRT1'.

BACKGROUND OF THE INVENTION

The present invention relates to a new and distinct variety of Shumard Oak tree (*Quercus Shumardii*) which I have named 'ACNRT1'.

Discovery

I discovered my new tree in the Spring, 2001 growing in a landscaped parking lot in the downtown area of Madison, Morgan County, Ga. The tree was grown from a 2" caliper field-grown tree which was purchased in the Spring, 1985 from a commercial nursery in Morgan County, Ga. This nursery is no longer in business and the original source of the tree is unknown.

Propagation

'ACNRT1' was asexually propagated, at my direction, in the Summer, 2002, by softwood cuttings using standard propagation procedures. The procedures were performed at a nursery in Oconee County, Ga. This propagation, and the resulting progeny, have proven the characteristics of my new variety to be firmly fixed. Further, these observations have confirmed my new variety represents a new and improved variety of Schumard Oak, as particularly evidenced by the upright, well-bunched habit with a central leader, and which can be reliably asexually propagated.

Uniqueness

'ACNRT1' was observed to have an upright, well-branched habit with a central leader. These characteristics distinguish my new tree from other typical seedlings of Shumard Oak.

Use

'ACNRT1' was observed for a period of time and is believed to be particularly useful in residential and commercial areas for street plantings and lawns, in parks, and in other large areas, as well as in smaller plating areas. The narrow habitat of the 'ACNRT1' makes it suitable for planting in areas not having space to accommodate a large spreading tree typical of the species, such as around buildings in commercial developments and in urban areas. The branching habit and central leader of the tree are an asset to growers who will benefit economically from a tree requiring less work to produce a quality, saleable tree with a sound structure. The tree has demonstrated an ability to be grown in urban area by virtue of its present location. It is now growing in a concrete island approximately 36 square feet in size and surrounded on all sides by a parking lot, parking lot driveway, and a sidewalk 4 feet from a city street. My new tree has survived and remained healthy in this environment since being planted in 1985.

SUMMARY OF THE INVENTION

Background

Seedling Shumard Oaks typically have a spreading canopy which is often open in youth. My new cultivar differs from the species in that it has an upright, well-branched habit with a central leader. Shumard Oaks are native to a geographical area ranging from Kansas to southern Michigan, eastwardly to North Carolina, and southerly to Texas and Florida. The tree grows well in USDA Hardiness Zones 5–9, and is considered a heat-resistant and drought-resistant tree. It prefers growing along streams, near swamps, or bodies of water in well drained soils. It will also grow at higher elevations, in rockier soil. Shumard Oak tolerates high pH soil (pH=7.0–8.0) as compared to most other oaks which prefer a more acidic soil.

Industry Representative

Cultivated Shumard Oak is represented in industry by seedling material. Shumard Oak is very difficult to propagate asexually, and to the inventor's knowledge, there are no other clonally propagated Shumard Oaks available. The parentage of my new tree is unknown, and because oaks are open-pollinated, it would be impossible to determine the male parent. From a genetics viewpoint, it can be assumed that either one or both of the parents have, or had, some combination of the form and branching habits displayed by my new tree. However, I have never seen another Shumard Oak that displays the upright, well-branched habit with a central leader as displayed by Shumard Oak tree 'ACNRT1'. Rather, the species is typically pyramidal and coarsely branched in youth, becoming spreading in maturity. Trees will generally reach a height and width of 40'–60' and so have a height to width ratio of 1.0. After 18 years, the current height of my tree is 30' and its width is 15'. Its height to width ratio is therefore 2.0. In my experience, no other seedling of Shumard Oak has displayed the growth habit of 'ACNRT1'. My tree is current 8.83" in caliper at a height of 4' above the ground. This low average caliper increase of 0.38" per year is likely due to its being planted in a non-irrigated urban site. Nursery grown Shumard Oaks in this area have an average annual caliper increase of 0.75" to 1.00". The progeny of my new tree have performed similar to typical seedlings Shumard Oaks when grown in a nursery setting.

DESCRIPTION OF THE DRAWINGS (PHOTOGRAPHS)

The accompanying photographs depict the color of the tree and the foliage of my new variety as nearly as is reasonably possible to make the same in a color illustration of this character.

FIG. 1 depicts the summer habit of the initially discovered tree of my new variety showing the narrow, upright branching habit and canopy. This photograph was taken in the Summer, 2003. At this time, the tree was approximately 23 years old, 30' tall, 15' wide, and 8.83" in caliper 4' above the ground.

DETAILED DESCRIPTION OF INVENTION

Figure 1:
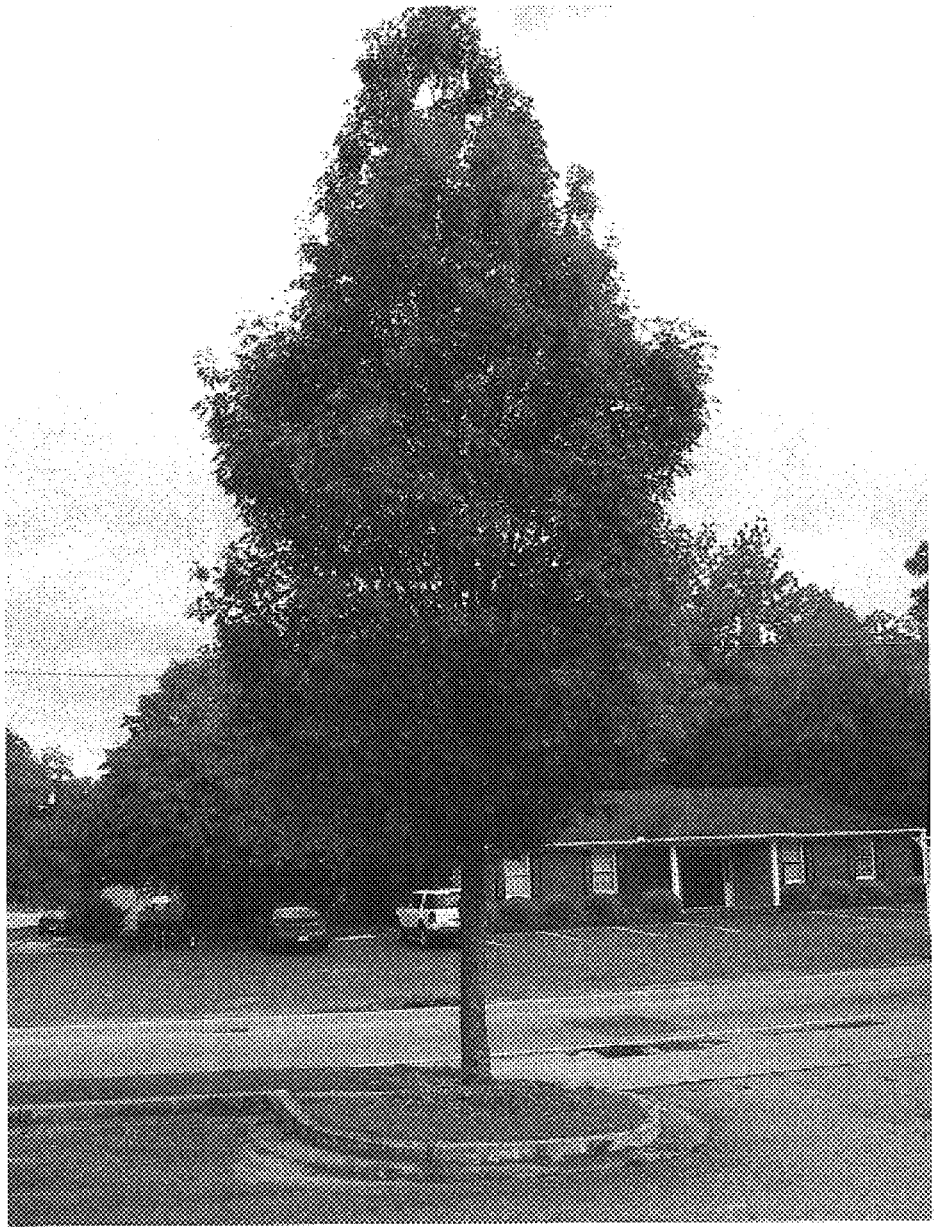
Figure 2:
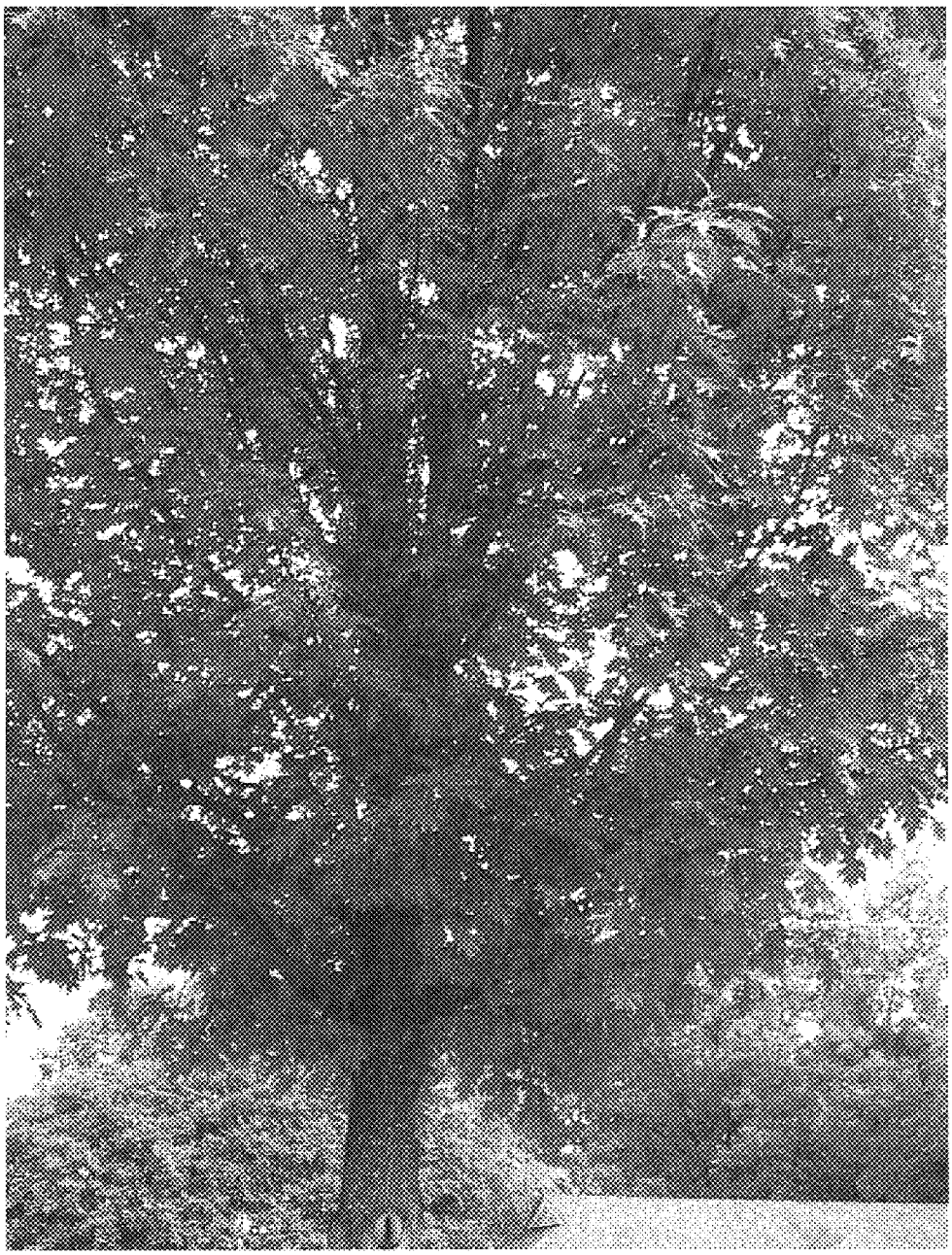
FIG. 2 depicts a close up of the branching habit and trunk of 'ACNRT1'.
Figure 3:
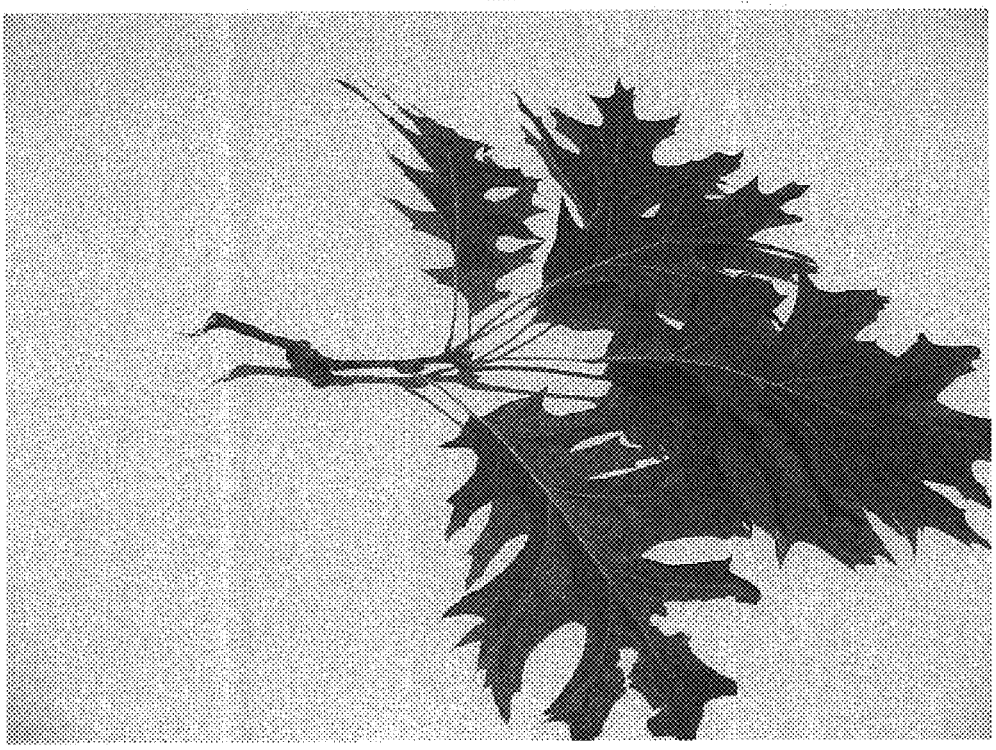
FIG. 3 depicts the upper leaf surface of 'ACNRT1'.
Figure 4:
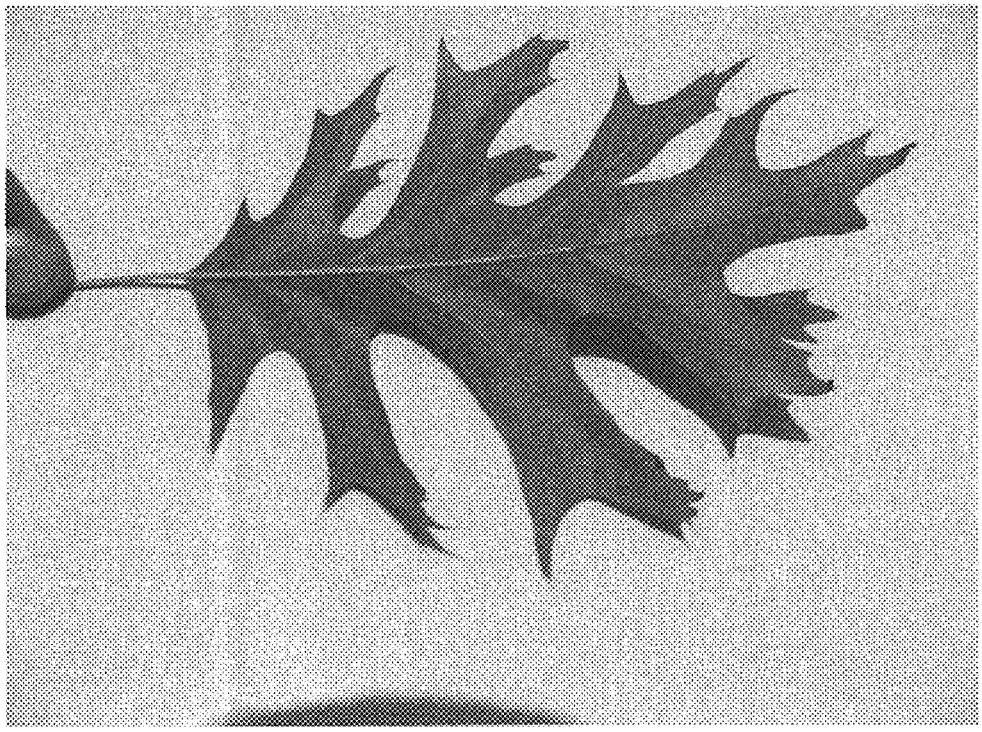
FIG. 4 depicts the lower leaf surface of 'ACNRT1'.

The following is a detailed description of my new variety of Shumard Oak with color terminology in accordance with The Royal Horticulture Society (R.H.S.) color chart, except where the context indicates a term having its ordinary dictionary meaning. My new tree has not been observed under all growing conditions, and variations may occur as a result of different growing conditions. All the progeny of my new variety, insofar as has been observed, have been identical in all of the characteristics described below.

Other than as set out below, as of this time, no other characteristics have been observed which are different from common Shumard Oaks which have been observed by the inventor.

Parentage: Seedling of unknown parentage grown from a 2" caliper field-grown tree purchased in the Spring, 1985 from Cedar Lane Farms in Morgan County, Ga.

Locality where grown and observed: A downtown parking lot in Madison, Morgan, Ga.

Leaves: typical of the species; i.e., alternate, simple, obovate to elliptic, acuminate, acute 7–9 lobes with deeply cut sinuses, 3–4" wide by 4–6" in height; dark green above like RHS Green 135A and glabrous below like RHS Green 137B; fall color typical of the species; yellow-bronze to slightly reddish; petiole: light green, 1½ to 2¼" long.

Buds: typical of the species; imbricate, angle-ovoid, ¼–⅜" long, glabrous, gray or straw-colored like RHS Greyed-green 197B, scales appear waxed.

Flowers: typical of the species; monoecious, appearing on old or new growth; male flowers are greenish-yellow, pendant and clustered in 3–6" long catkins; individual flowers comprise a 4–7 lobed calyx which encodes 6 or more stamens; staminate catkins emerge with the leaves and offer no floral display. Female flowers are inconspicuous, brownish-green in color, occuring solitary or in few- to many-flowered spikes from the axils of the new leaves; individual flowers consist of a 6-lobed calyx surrounding a 3-celled ovary, the whole of which is partially enclosed in an involucre. Both male and female flowers are apetalous and asepalous.

Fruit: an acorn, typical of the species; ovate, ¾–1" long and ½–¾" side, short-stalked and covered only at the base by a gray-brown (RHS 199A) hemispherical-shaped involucral cap which covers approximately ⅓ of the base of the acorn which is gray-orange (RHS 165A). The nut is striated with dark brown lines (RHS 200A).

Stem: typical of the species; gray-brown, glabrous; older stems are greenish brown and have an onion-like sheathing of epidermis.

Trunk: typical of the species; graying like RHS Greyed-green 198A and smooth, developing narrow, shallow ridges and furrows with age, like RHS Greyed-green 188A and RHS Greyed-green 197C.

Branching: very upright ascending branches, emerging at, and maintaining, a 30° angle from the trunk.

Growth habit: narrow pyramidal with upright branching.

Root system: typical of the species, coarse but transplanting well; progeny have proved to be typical of the species.

Vigor: typical of the species; in production, averages up to 1" caliper increase per year.

Diseases: no disease problems have been observed on the parent or any progeny. This is typical of the species.

Pests: no insect problems have been observed on the parent or progeny. This is typical of the species.

The parent of my new Shumard Oak tree 'ACNRT1' has not been cloned.

What is claimed is:

1. A new and distinct variety of Shumard Oak tree named 'ACNRT1' substantially as shown and described, characterized particularly as to novelty by its upright, well-branched habit with a central leader.

* * * * *